US012718604B2

(12) United States Patent
Yamamoto et al.

(10) Patent No.: US 12,718,604 B2
(45) Date of Patent: Aug. 25, 2026

(54) CELL IMAGE ANALYSIS SYSTEM

(71) Applicant: SHIMADZU CORPORATION, Kyoto (JP)

(72) Inventors: Shuhei Yamamoto, Kyoto (JP); Ryuji Sawada, Kyoto (JP); Takeshi Ono, Kyoto (JP); Hiroaki Tsushima, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 245 days.

(21) Appl. No.: 18/699,096

(22) PCT Filed: Jun. 22, 2022

(86) PCT No.: PCT/JP2022/024899
§ 371 (c)(1),
(2) Date: Apr. 5, 2024

(87) PCT Pub. No.: WO2023/058271
PCT Pub. Date: Apr. 13, 2023

(65) Prior Publication Data

US 2025/0232600 A1 Jul. 17, 2025

(30) Foreign Application Priority Data

Oct. 8, 2021 (JP) ................................ 2021-166370

(51) Int. Cl.
*G06V 20/00* (2022.01)
*G06V 20/69* (2022.01)
*G16H 30/40* (2018.01)

(52) U.S. Cl.
CPC .......... *G06V 20/698* (2022.01); *G16H 30/40* (2018.01)

(58) Field of Classification Search
CPC .... G06V 20/698; G06V 10/945; G06V 20/69; G16H 30/40; G16H 50/20; G16H 50/50;
(Continued)

(56) References Cited

U.S. PATENT DOCUMENTS

2010/0070904 A1* 3/2010 Zigon ................ G06V 10/7625 715/854
2011/0269154 A1* 11/2011 Fantl ................ G01N 33/57505 435/7.24
(Continued)

FOREIGN PATENT DOCUMENTS

JP 2021-64115 A 4/2021

OTHER PUBLICATIONS

Jennifer Wilshire et al., "FlowJo Basic Tutorial", Tree Star, 2002, Version 1 1, pp. 1-26 (26 pages total) (Year: 2002).*
(Continued)

*Primary Examiner* — Van D Huynh
(74) *Attorney, Agent, or Firm* — Sughrue Mion, PLLC

(57) ABSTRACT

A cell image analysis system (100) according to this invention includes a data tree creator (11), a graph creator (12), and a display controller (13). The display controller is configured to display a second data tree (24*b*) that is different from a first data tree (24*a*), and has horizontal and vertical axis parameters that are common to the first data tree, and, when the second data tree is selected by a user, to update a graph by adding the analysis results of cell images (30) that are included in the second data tree selected by the user to the graph.

12 Claims, 8 Drawing Sheets

(58) Field of Classification Search
CPC ........... G06T 11/26; G06T 2207/10056; G06T 2207/30024; C12M 41/36
See application file for complete search history.

(56) References Cited

U.S. PATENT DOCUMENTS

| | | | | |
|---|---|---|---|---|
| 2015/0262396 | A1* | 9/2015 | Devarajan | G06F 3/0486 345/440.1 |
| 2020/0401798 | A1* | 12/2020 | Foncubierta Rodriguez | G06F 16/51 |
| 2021/0110536 | A1 | 4/2021 | Akazawa | |
| 2021/0217486 | A1* | 7/2021 | Zaaijer | G16B 10/00 |
| 2023/0016958 | A1* | 1/2023 | Wakui | G06V 10/454 |
| 2024/0169519 | A1* | 5/2024 | Tjon | G16H 50/20 |

OTHER PUBLICATIONS

Jennifer Wilshire et al., “FlowJo Basic Tutorial”, Tree Star, 2002, Version 1.1, pp. 1-26 (26 pages total).

Extended European Search Report dated Jul. 18, 2025 from the European Patent Office in Application No. 22878144.9.

Shimadzu Corporation, Web application supporting cellular observations Cell Pocket, “Understand data quickly”, “Analysis example”, “Seven steps from deep learning to analysis with Cell Pocket.”, Nov. 24, 2020, 20 pages, <URL https://web.archive.org/web/20201124205624/https:/www.an.shimadzu.co.jp/bio/cell/cellpocket/features.html#cp03>.

Shimadzu Corporation launches, “Web application supporting cellular observations Cell Pocket”, management and analysis software for cell image that evolve with AI (deep learning), Nov. 5, 2020, 7 pages, <URL : https://www.shimadzu.co.jp/news/press/216g9q6kb5olyoec.html>.

Written Opinion for PCT/JP2022/024899, dated Sep. 13, 2022.

International Search Report for PCT/JP2022/024899, dated Sep. 13, 2022.

Japanese Office Action dated Mar. 5, 2025 in Application No. 2023-552693.

* cited by examiner

10

PROCESSOR

DATA TREE CREATOR —11

GRAPH CREATOR —12

DISPLAY CONTROLLER —13

DATA TREE SEARCHER —14

FILE OUTPUT —15

CELL IMAGE ANALYSIS SYSTEM

TECHNICAL FIELD

The present invention relates to a cell image analysis system.

BACKGROUND ART

Techniques for analyzing a cell image are disclosed in the art. Such a technology is disclosed in Japanese Patent Laid-Open Publication No. JP 2021-64115, for example.

The above Japanese Patent Laid-Open Publication No. JP 2021-64115 discloses a technique for analyzing a cell image captured by using a microscope. Specifically, the above Japanese Patent Laid-Open Publication No. JP 2021-64115 discloses calculation of an entire area of a cell from the cell image, and calculation of a ratio of the cell area to an entire area of the cell image captured.

PRIOR ART

Patent Document

Patent Document 1: Japanese Patent Laid-Open Publication No. JP 2021-64115

SUMMARY OF THE INVENTION

Problems to be Solved by the Invention

Although not stated in the above Japanese Patent Laid-Open Publication No. JP 2021-64115, in order to manage cell images, a data tree that classifies the cell images based on a hierarchical structure is created in some cases. Also, in order to display analysis results of cell images for each data tree, graphs representing the analysis results of the cell images are created for the data tree in some cases. In such cases, although a plurality of data trees are created in the cell analysis system, the cell analysis system can merely display the graphs for each data tree but data trees different from each other cannot be easily compared with each other. For this reason, it is desired to easily compare different data trees with each other in a case in which cell images are managed by using data trees.

The present invention is intended to solve the above problem, and one object of the present invention is to provide a cell image analysis system capable of easily comparing different data trees with each other in a case in which cell images are managed by using data trees.

Means for Solving the Problems

In order to attain the aforementioned object, a cell image analysis system according to one aspect of the present invention includes a data tree creator configured to create a plurality of data trees relating to cell images by classifying the cell images into a plurality of groups each of which includes the cell images that have common classification information; a data tree storage configured to store the plurality of data trees created by the data tree creator, and a data tree storage area that stores the data trees created by the data tree creator; a graph creator configured to create a graph relating to a first data tree that is selected by a user, and having classification information of a bottom layer or a second layer from the bottom layer of the first data tree as a horizontal axis parameter and analysis results of the cell images that are included in the first data tree as a vertical axis parameter; and a display controller configured to display the graph created by the graph creator, wherein the display controller is configured to display a second data tree that is different from the first data tree and has common horizontal and vertical axis parameters to the first data tree in the plurality of data trees stored in the data tree storage to be selectable by the user, and, when the second data tree is selected by the user, to update the graph by adding the analysis results of the cell images that are included in the second data tree selected by the user to the graph.

Effect of the Invention

In the cell image analysis system according to the one aspect, the graph is updated by adding the analysis results of the cell images that are included in the second data tree, which is different from the first data tree and has common horizontal and vertical axis parameters to the first data tree to the graph. Accordingly, it possible to display analysis results of the cell images that are included in the first data tree, and the analysis results of the cell images that are included in the second data tree, which is different from the first data tree and has common horizontal and vertical axis parameters to the first data tree on the same graph to compare them with each other. Consequently, it is possible to easily compare different data trees with each other in a case in which cell images are managed by using data trees.

Although it is conceivable that a user adds data of the second data tree to the first data tree and creates a new data tree in order to compare the different data trees, an additional operation is required for the user to add the data of the second data tree to the first data tree in such a case of new data tree creation. Contrary to this, the graph is updated by adding the analysis results of the cell images that are included in the second data tree, which is different from the first data tree and has common horizontal and vertical axis parameters to the first data tree, as discussed above. Accordingly, because the graph is automatically updated when the second data tree is selected by the user, the user can easily compare the different data trees with each other without such an additional operation for adding the data of the second data tree to the first data tree.

Also, because the user necessarily appropriately aligns the vertical and horizontal axes of the graph when comparing the different data trees with each other, an additional operation is required for the user to appropriately align the vertical and horizontal axes of the graph in this case. Contrary to this, as discussed above, the graph is updated by adding the analysis results of the cell images that are included in the second data tree, which is different from the first data tree and has common horizontal and vertical axis parameters to the first data tree, to the graph as discussed above. Accordingly, because the graph is automatically updated when the second data tree is selected by the user, the user can easily compare the different data trees with each other without such an additional operation for appropriately aligning the vertical and horizontal axes of the graph.

The embodiment of the present invention is described below based on the drawings.

Refer to FIGS. 1 to 9 to explain the structure of the cell image analysis system 100 by one embodiment.

MODES FOR CARRYING OUT THE INVENTION (Cell Image Analysis System)

Figures 1, 2:
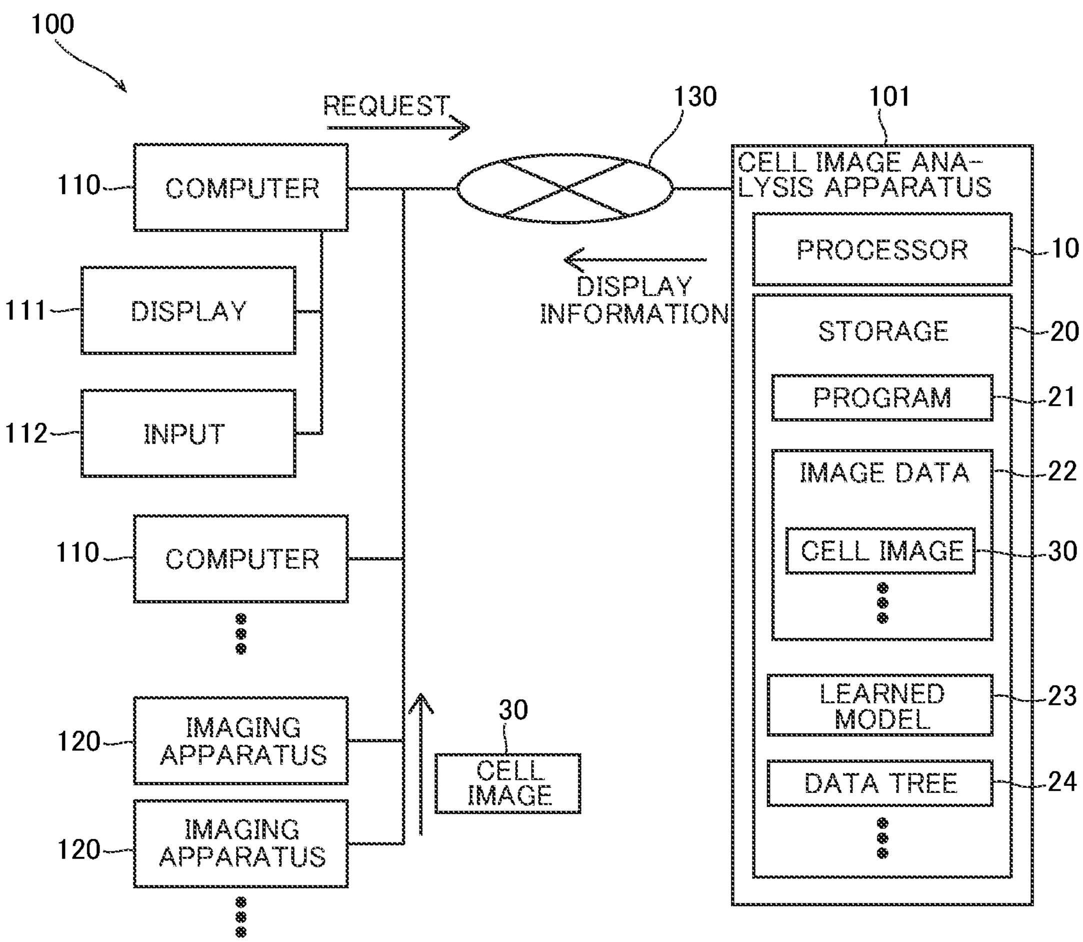
FIG. 1 is a block diagram showing a cell image analysis system according to one embodiment.
FIG. 2 is a functional block diagram showing a cell image analysis apparatus according to the one embodiment.

The cell image analysis system 100 shown in FIG. 1 is a single system that allows users who cultivate cells, etc. integrally to capture cell images 30, to apply analysis processing to the cell images 30, and to peruse images to which the analysis processing is applied.

(Outline of Cell Image Analysis System)

The cell image analysis system 100 includes a cell image analysis apparatus 101, a computer 110, and an imaging apparatus 120.

The cell image analysis system 100 shown in FIG. 1 is illustratively constructed of a client-server model. The computer 110 serves as a client terminal in the cell image analysis system 100. The cell image analysis apparatus 101 serves as a server in the cell image analysis system 100. The cell image analysis apparatus 101, the computer 110, and the imaging apparatus 120 are connected through a network 130, and can communicate with each other through the network. The cell image analysis apparatus 101 performs various types of information processing in response to requests (processing requests) from the computer 110 operated by users. The cell image analysis apparatus 101 is configured to apply analysis processing to the cell images 30 in response to request and to transmit images to which the analysis processing is applied to the computer 110. A graphical user interface (GUI) is displayed on a display 111 of the computer 110, and is configured to accept instructions provided to the cell image analysis apparatus 101 and to display analysis results analyzed by the cell image analysis apparatus 101 and images after the analysis.

The network 130 connects the cell image analysis apparatus 101, the computer 110, and the imaging apparatus 120 to each other so that they can communicate with each other. The network 130 can be LAN (Local Area Network) configured in the facility, for example. The network 130 can be the Internet, for example. In a case in which the network 130 is the Internet, the cell image analysis system 100 can be a system configured in a cloud computing form.

The computer 110 is a so-called personal computer including a processor and a storage. The display 111 and an input 112 are connected to the computer 110. For example, the display 111 is a liquid crystal display. Alternatively, the display 111 can be an electro-luminescence display, a projector, or a head-mounted display. For example, the input 112 is an input device including a computer mouse and a key-board.

Alternatively, the input 112 can be a touch panel. The cell image analysis system 100 can include one or more computers 110.

The Imaging apparatus 120 includes a microscope, and is configured to generate the cell images 30. The imaging apparatus 120 can send the generated cell images 30 to the computer 110 and/or the cell image analysis apparatus 101 through the network 130. The imaging apparatus 120 is configured to capture microscopic images of cells. The imaging apparatus 120 can use imaging methods such as bright-field observation, dark-field observation, phase contrast observation, differential interference observation, and the like for imaging. One or more of the imaging apparatuses 120 are used in accordance with imaging methods. The cell image analysis system 100 can include one or more imaging apparatuses 120.

The cell image analysis apparatus 101 includes a processor 10, such as CPU (Central Processing Unit), FPGA (Field-Programmable Gate Array), and ASIC (Application Specific Integrated Circuit). The cell image analysis apparatus 101 is configured to perform arithmetic processing by using the processor 10 by executing a predetermined program 21.

The cell image analysis apparatus 101 includes a storage 20. The storage 20 includes a non-volatile storage device. For example, the non-volatile storage device is a hard disk drives, solid state drives, and the like. The storage 20 is configured to store various programs 21 to be executed by the processor 10. The storage 20 is configured to store image data 22. The image data 22 includes the cell images 30 captured by the Imaging apparatus 120, and various processed images generated by applying image processing to the cell images 30. The storage 20 stores a learned model 23 that has learned to acquire cell areas from the cell images 30. Also, the storage 20 stores data trees 24 including the cell images 30 classified based on a hierarchical structure. The data trees 24 will be described later. The storage 20 is an example of a "data tree storage" in the claims.

The cell image analysis apparatus 101 is configured to analyze the cell images 30 and to display analysis results in response to requests from the computer 110. In the analysis, the cell image analysis apparatus 101 acquires features based on the cell images 30. In the displaying of analysis results, the cell image analysis apparatus 101 generates display information such as a graph 50, which will be described later. The cell image analysis apparatus 101 transmits the display information generated to the computer 110. The computer 110 displays a screen display based on the display information on the display 111 when receiving the display information.

(Configuration of Cell Image Analysis Apparatus)

As shown in FIG. 2, the processor 10 of the cell image analysis apparatus 101 includes a data tree creator 11, a graph creator 12, and a display controller 13, a data tree searcher 14, and a file output 15 as function blocks. In other words, the processor 10 is configured to execute the program 21 stored in the storage 20 to serve as the data tree creator 11, the graph creator 12, and the display controller 13, the data tree searcher 14, and the file output 15.

Figure 3:
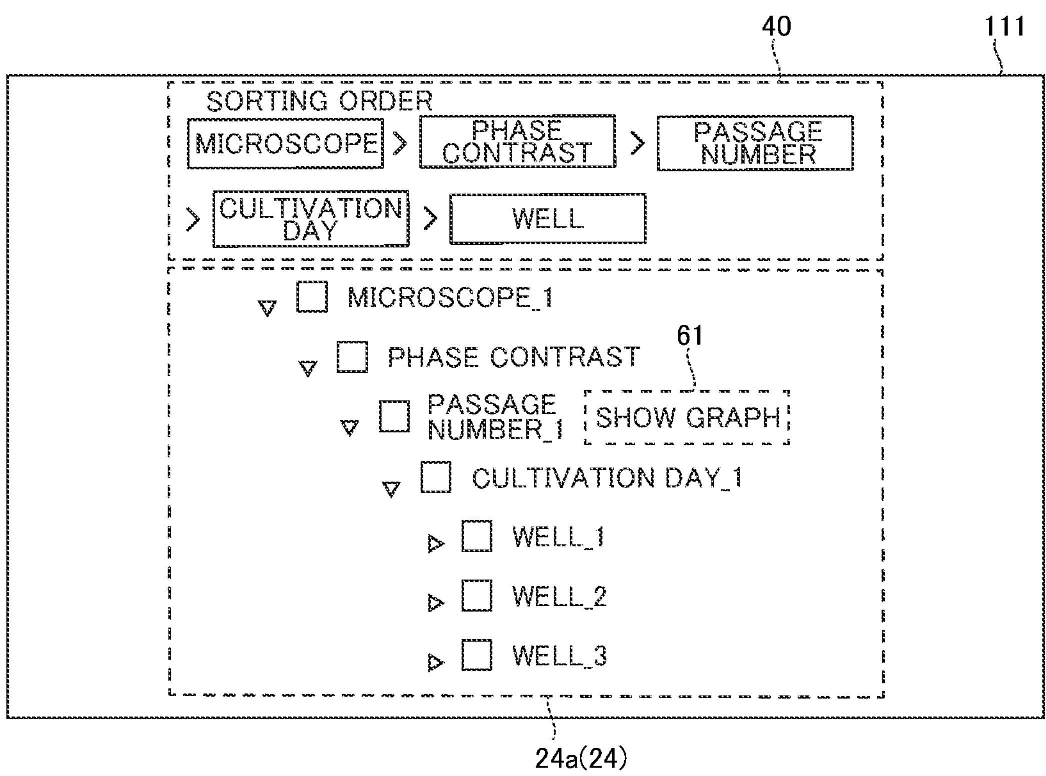
FIG. 3 is a diagram illustrating a data tree of the cell image analysis apparatus according to the one embodiment.

As shown in FIGS. 2 and 3, the data tree creator 11 is configured to create a plurality of data trees 24 relating to cell images 30 by classifying the cell images 30 into a plurality of groups each of which includes the cell images that have common classification information 40. A plurality of types of classification information 40 are associated with each cell image 30. The data tree creator 11 is configured to create the virtual data tree 24 having a hierarchical structure by grouping the cell images 30 based on the classification information 40 associated with the cell images 30. Also, the data tree creator 11 is configured to create the virtual data tree 24 having a hierarchical structure by grouping the cell images in stages based on a sorting order (priority) specified for each of the plurality of types of classification information 40. Also, the display controller 13 is configured to transmit the data tree 24 created by the data tree creator 11 to the computer 110 so as to display the data tree on the display 111. In this embodiment, the data tree 24 is formed as the virtual data tree 24 having the hierarchical structure on a screen of the display 111.

In an exemplary screen shown in FIG. 3, the imaging apparatus 120 (identification number of microscope) that captured the cell image 30, the phase contrast observation that captured the cell image 30, the number of passages of the cells, the number of cultivation days of the cells, and a well (well number) that is a recessed part in which the cells were cultivated are specified as the classification information 40. Also, the sorting order is set as the order of the imaging apparatus 120 (identification number of microscope), the phase contrast observation, the number of passages, the cultivation days, and the well (well number). In this case, the data tree creator 11 creates a five-layer data tree 24 including the imaging apparatus 120 as the top layer, and the well as the bottom layer. One or more cell images 30 are assigned to each of "Well 1", "Well 2", and "Well 3" in the bottom layer.

Also, the data tree creator 11 is configured be able to change the sorting order (priority) of the classification information 40 included in the data tree 24. Specifically, the data tree creator 11 is configured to change the sorting order of the hierarchical structure of the data tree 24 by changing the sorting order of the classification information 40 on the screen of the display 111 in accordance with on an instruction input through the input 112 by a user. Also, the data tree creator 11 is configured to change the sorting order of the hierarchical structure of the data tree 24 to delete a part of the sorting order by deleting the part of the sorting order of the classification information 40 on the screen of the display 111 in accordance with on an instruction input through the input 112 by the user. Also, the display controller 13 is configured to display the changed data tree 24 on the display 111. Also, the data tree 24 created by the data tree creator 11 is stored in the storage 20 associated with the data tree being associated with a project and cultivation conditions relating to cell cultivation.

Figure 4:
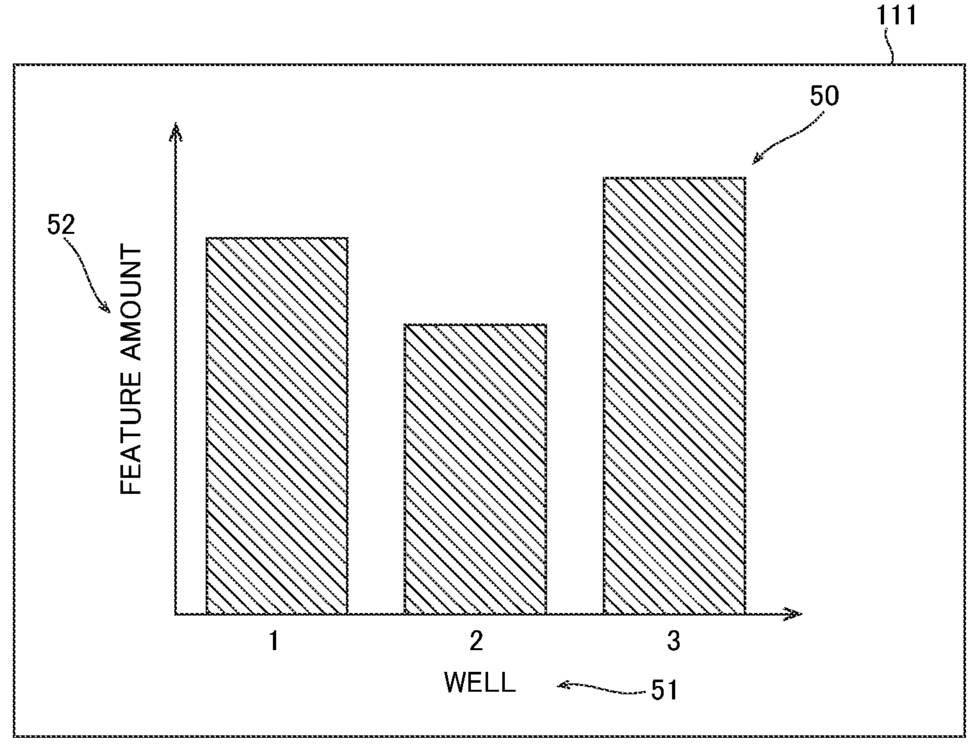
FIG. 4 is a diagram illustrating a graph relating to the data tree of the cell image analysis apparatus according to the one embodiment.

As shown in FIGS. 2 to 4, the graph creator 12 is configured to create the graph 50 relating to a first data tree 24*a* that is selected from the plurality of data trees by the user, and having classification information 40 (in this case, "well") of the bottom layer the first data tree 24*a* as a horizontal axis parameter 51, and analysis results of the cell images 30 that are included in the first data tree 24*a* as a vertical axis parameter 52. Specifically, the graph creator 12 is configured to create the graph 50 if an indication item 61 "Show the graph" on the screen of the display 111 is selected in accordance with an instruction input through the input 112 by the user. Also, the display controller 13 is configured to transmit the graph 50 created by the graph creator 12 to the computer 110 so as to display the graph on the display 111.

In this embodiment, the horizontal axis parameter 51 is accessory information on cell cultivation or imaging. The horizontal axis parameter 51 is not specifically limited, but can be cultivation days, wells, passages, microscope, imaging method, microscope channels, cell type, cultivation medium, cell line, ground substance, inductor, oxygen concentration, carbon dioxide concentration, temperature, or the like, for example. The vertical axis parameter 52 corresponds to feature amounts acquired based on the cell images 30. The vertical axis parameter 52 is not specifically limited, but can be the number of cells, morphological information of the cells (length, roundness, radii, aspect ratios, etc.), a percentage of differentiated/undifferentiated cells, similarity of cell texture, area information of cells, or the like.

Figure 5:
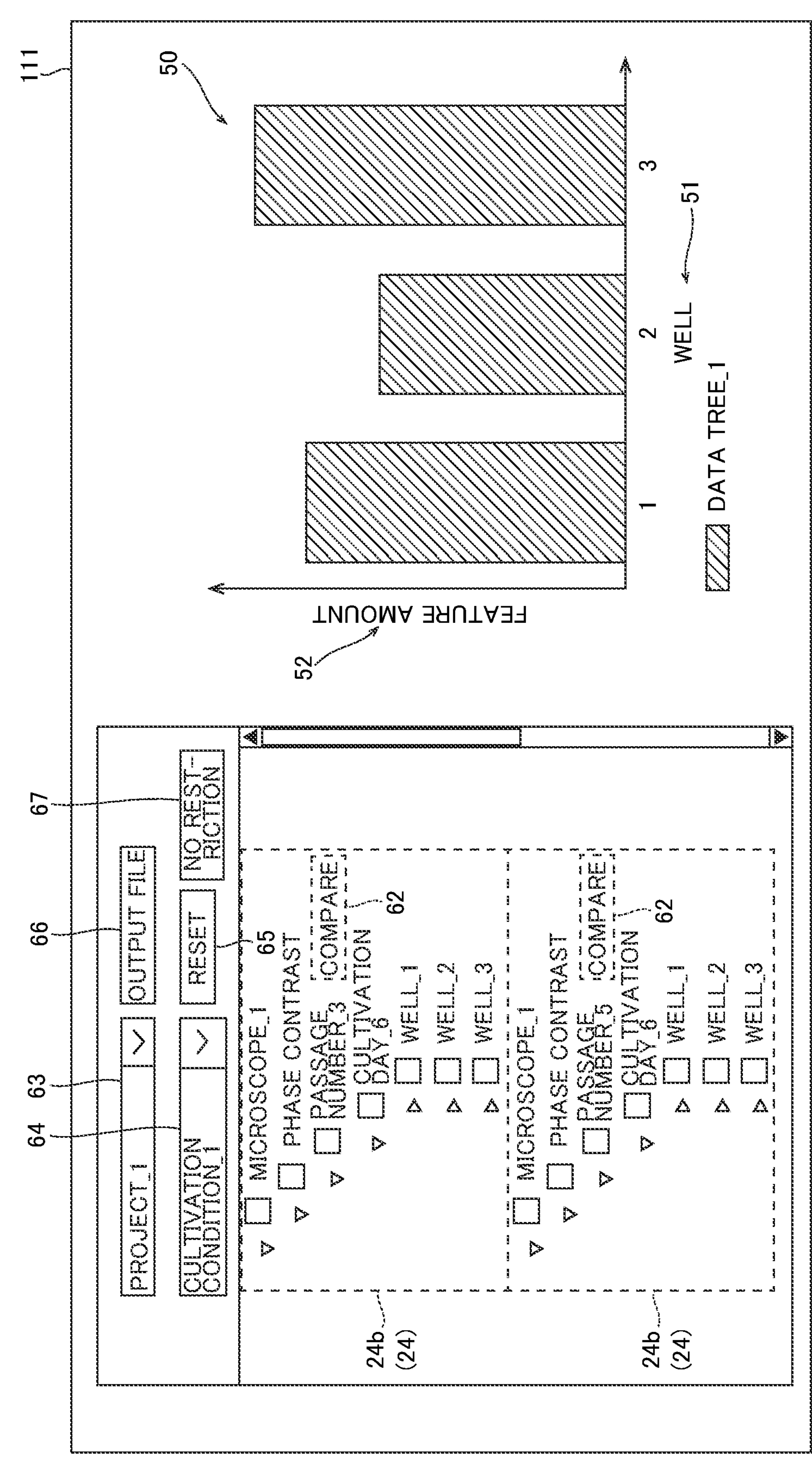
FIG. 5 is a diagram illustrating a process for searching in the data tree of the cell image analysis apparatus according to the one embodiment.
Figure 6:
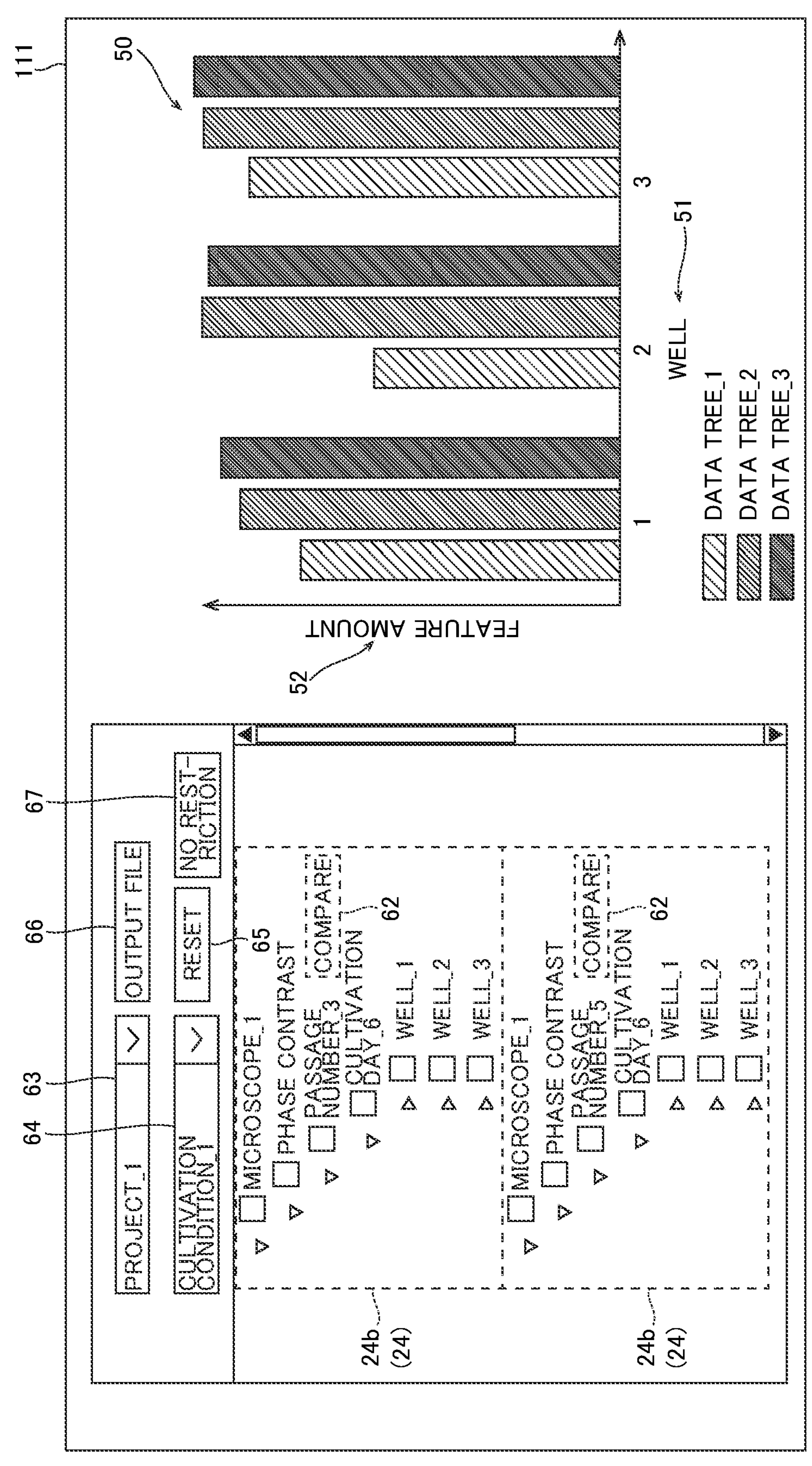
FIG. 6 is a diagram illustrating a process for updating in the graph of the cell image analysis apparatus according to the one embodiment.

In this embodiment, as shown in FIGS. 5 and 6, the display controller 13 is configured to display a second data tree 24*b* that is different from the first data tree 24*a* and has the horizontal axis parameter 51 and the vertical axis parameter 52 that are common to the first data tree 24*a* in the plurality of data trees 24 stored in the storage 20 to be selectable by the user, and, when the second data tree 24*b* is selected by the user, to update the graph 50 by adding the analysis results of the cell images 30 that are included in the second data tree 24*b* selected by the user to the graph 50.

In other words, the display controller 13 is configured to display comparative past cases (second data tree 24*b*) corresponding to the first data tree 24*a* to be selectable by the user, and to update the graph 50 to be able to compare analysis results of the cell images 30 that are included in the comparative past cases (second data tree 24*b*) selected by the user with the analysis results of the cell images 30 that are included in the first data tree 24*a*. Based on the updated graph 50, the user can compare validities of tendencies of the analysis results between the data trees 24 having the same horizontal and vertical axis parameters 51 and 52, or can compare differences in the analysis results between the data trees, for example. Also, the display controller 13 is configured to update the graph 50, if a plurality of (two in FIG. 6) second data trees 24*b* are selected by the user, by adding the analysis results of the cell images 30 that are included in the plurality of second data trees 24*b* selected by the user to the graph 50.

Specifically, the display controller 13 is configured to display, on the display 111, an indication item 62 "Compare" corresponding to an instruction of the user to add the analysis results of the cell images 30 that are included in the second data tree 24*b* to the graph 50. Specifically, the graph creator 12 is configured to re-create the graph 50, if the indication item 62 "Compare" on the screen of the display 111 is selected in accordance with an instruction input through the input 112 by the user, by adding the analysis results of the cell images 30 that are included in the second data tree 24*b* selected by the user to the graph 50. Also, the display controller 13 is configured to transmit the graph 50 re-created by the graph creator 12 to the computer 110 so as to update the graph 50 displayed on the display 111.

Also, the graph creator 12 is configured to re-create the graph 50, if an indication item 62 "Compare" corresponding to another second data tree 24*b* on the screen of the display 111 is selected in accordance with an instruction input through the input 112 by the user with the analysis results of the cell images 30 that are included in the second data tree 24*b* being added to the graph 50, by further adding the analysis results of the cell images 30 that are included in the second data tree 24*b* selected by the user to the graph 50. Also, the display controller 13 is configured to transmit the graph 50 that is re-created by further adding the another second data tree 24*b* by the graph creator 12 to the computer 110 so as to update the graph 50 displayed on the display 111. The user can add analysis results of cell images 30 of any number of the second data trees 24*b* to the graph 50.

In this embodiment, the data tree searcher 14 is configured to search for the second data tree 24*b* in the plurality of data trees 24 stored in the storage 20. Also, the display controller 13 is configured to display the second data tree 24*b* searched by the data tree searcher 14 so as to be selectable by the user. In this case, the display controller 13 is configured to display the second data tree 24*b* searched by the data tree searcher 14 in list form.

In this embodiment, the data tree searcher 14 is configured to be able to search for the second data tree 24*b* in the plurality of data trees 24 stored in the storage 20 with the project and the cultivation conditions relating to cell cultivation being specified as search criteria. Also, the display controller 13 is configured to display the second data tree 24*b* searched by the data tree searcher 14 with the search criteria being specified so as to be selectable by the user.

The display controller 13 is configured to display, on the display 111, a pull-down indication item 63 for selecting a project type (project name), and a pull-down indication item 64 for selecting a cultivation condition type (cultivation condition name). Also, the data tree searcher 14 is configured to search, if the project and cultivation condition are selected in the indication items 63 and 64 on the display screen of the display 111 in accordance with instructions input through the input 112 by the user, for the second data tree 24*b* corresponding to the project and cultivation condition selected. That is, the data tree searcher 14 is configured to search for the second data tree 24*b* associated with the project selected and with the cultivation condition selected, and having the horizontal axis parameter 51 and the vertical axis parameter 52 that are common to the first data tree 24*a*. The name of the project and the names of the cultivation conditions are previously specified by the user.

For example, a case in which the user specifies (selects) a project different from the first data tree 24*a* and a cultivation condition common to the first data tree as the search criteria is considered. In this case, the data tree searcher 14 searches for the second data tree 24*b* in the plurality of data trees 24 stored in the storage 20 with the project different from the first data tree 24*a* and the cultivation condition common to the first data tree being specified as the search criteria. Also, the display controller 13 is configured to display the second data tree 24*b* that corresponds to the project different from the first data tree 24*a* and the cultivation condition common to the first data tree searched by the data tree searcher 14 with the project different from the first data tree 24*a* and the cultivation condition common to the first data tree being specified as the search criteria.

Also, for example, a case in which the user specifies (selects) a project common to the first data tree 24*a* and a cultivation condition different from the first data tree as the search criteria is considered. In this case, the data tree searcher 14 searches for the second data tree 24*b* in the plurality of data trees 24 stored in the storage 20 with the project common to the first data tree 24*a* and the cultivation condition different from the first data tree being specified as the search criteria. Also, the display controller 13 is configured to display the second data tree 24*b* that corresponds to the project common to the first data tree 24*a* and the cultivation condition different from the first data tree searched by the data tree searcher 14 with the project different from the first data tree 24*a* and the cultivation condition common to the first data tree being specified as the search criteria. In addition, the user can specify a project and a cultivation condition common to the first data tree 24*a* as search criteria, and can specify a project and a cultivation condition different from the first data tree 24*a* as search criteria.

The display controller 13 is configured to update the graph 50 by adding the analysis results of the cell images 30 that are included in the second data tree 24*b* selected by the user in a color different from the analysis results of the cell images 30 that are included in the first data tree 24*a* to the graph 50. For example, in a case in which the analysis results of the cell images 30 that are included in the first data tree 24*a* are displayed in red in the graph 50, the display controller 13 displays the analysis results of the cell images 30 that are included in the second data tree 24*b* in green, which is different from the red, in the graph 50.

Also, in a case in which, after the analysis results of the cell images 30 that are included in the second data tree 24*b* have been added to the graph 50, analysis results of the cell images 30 that are included in another second data tree 24*b* are further added to the graph 50, the display controller 13 is configured to update the graph 50 by further adding the analysis results of the cell images 30 that are included in the another second data tree 24*b* in a color different from the analysis results of the cell images 30 that are included in the first data tree 24*a* and the analysis results of the cell images 30 that are included in the second data tree 24*b* and have been added to the graph 50. For example, in a case in which the analysis results of the cell images 30 that are included in the first data tree 24*a* are displayed in red and the analysis results of the cell images 30 that are included in the second data tree 24*b* and have been added are displayed in green in the graph 50, the display controller 13 displays the analysis results of the cell images 30 that are included in the another second data tree 24*b* in blue, which is different from the red and the green, in the graph 50.

In this embodiment, the display controller 13 is configured to update the graph 50, when the user provides an instruction to delete the analysis results that are included in the second data tree 24*b* and have been added to the graph 50, by deleting the analysis results of the cell images 30 that are included in the second data tree 24*b* and have been added to the graph 50 from the graph 50. Specifically, the display controller 13 is configured to display, on the display 111, an indication item 65 "Reset" corresponding to an instruction to delete the analysis results that are included in the second data tree 24*b* and have been added to the graph 50. Also, the graph creator 12 is configured to re-create the graph 50, if the indication item 65 "Reset" on the screen of the display 111 is selected in accordance with an instruction input through the input 112 by the user, by deleting all the analysis results of the cell images 30 that are included in the second data tree 24*b* that have been added to the graph 50 from the graph 50. In other words, the graph creator 12 is configured to re-create the graph 50 by deleting all the analysis results of the cell images 30 that are included in the second data tree 24*b* that have been added to the graph 50 from the graph 50 so as to return the graph to an initial state (state shown in FIG. 5). Also, the display controller 13 is configured to transmit the graph 50 re-created by the graph creator 12 to the computer 110 so as to update the graph 50 displayed on the display 111.

Figure 7:
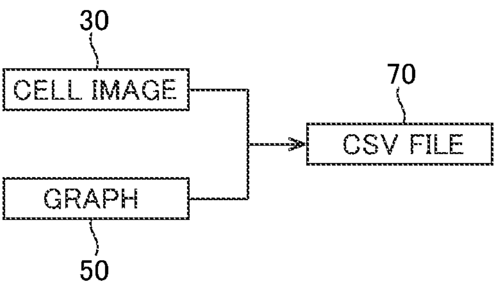
FIG. 7 is a diagram illustrating a process for outputting a CSV file of the cell image analysis apparatus according to the one embodiment.

In this embodiment, as shown in FIG. 7, the file output 15 is configured to output the cell images 30 that serve as a basis for the graph 50 including the added analysis results of the cell images 30 that are included in the second data tree 24*b*, and the graph 50 that includes the added analysis results of the cell images 30 that are included in the second data tree 24*b* as a CSV (Comma Separated Value) file 70, which includes values separated with commas. In other words, the file output 15 is configured to acquire the cell images 30 that serve as a basis for the graph 50 including the first data tree 24*a* and the cell image 30 that serve as a basis for the graph including the second data tree 24*b*, and the graph 50 as numerical data separated with commas, and to output the CSV file 70 including the cell images 30 and the graph 50 acquired as numerical data to the computer 110. Also, the file output 15 is configured to output the CSV file 70 to the computer 110 if an indication item 66 "Output File" on the screen of the display 111 is selected in accordance with an instruction input through the input 112 by the user.

In this embodiment, the file output 15 is configured to output the CSV file 70 with additional information including information on projects and cultivation conditions relating to cell cultivation. The additional information is not specifically limited, but can include project names, cultivation condition names, classification information 40 (microscope, phase contrast observation, number of passages, cultivation days, wells, etc.).

Figure 8:
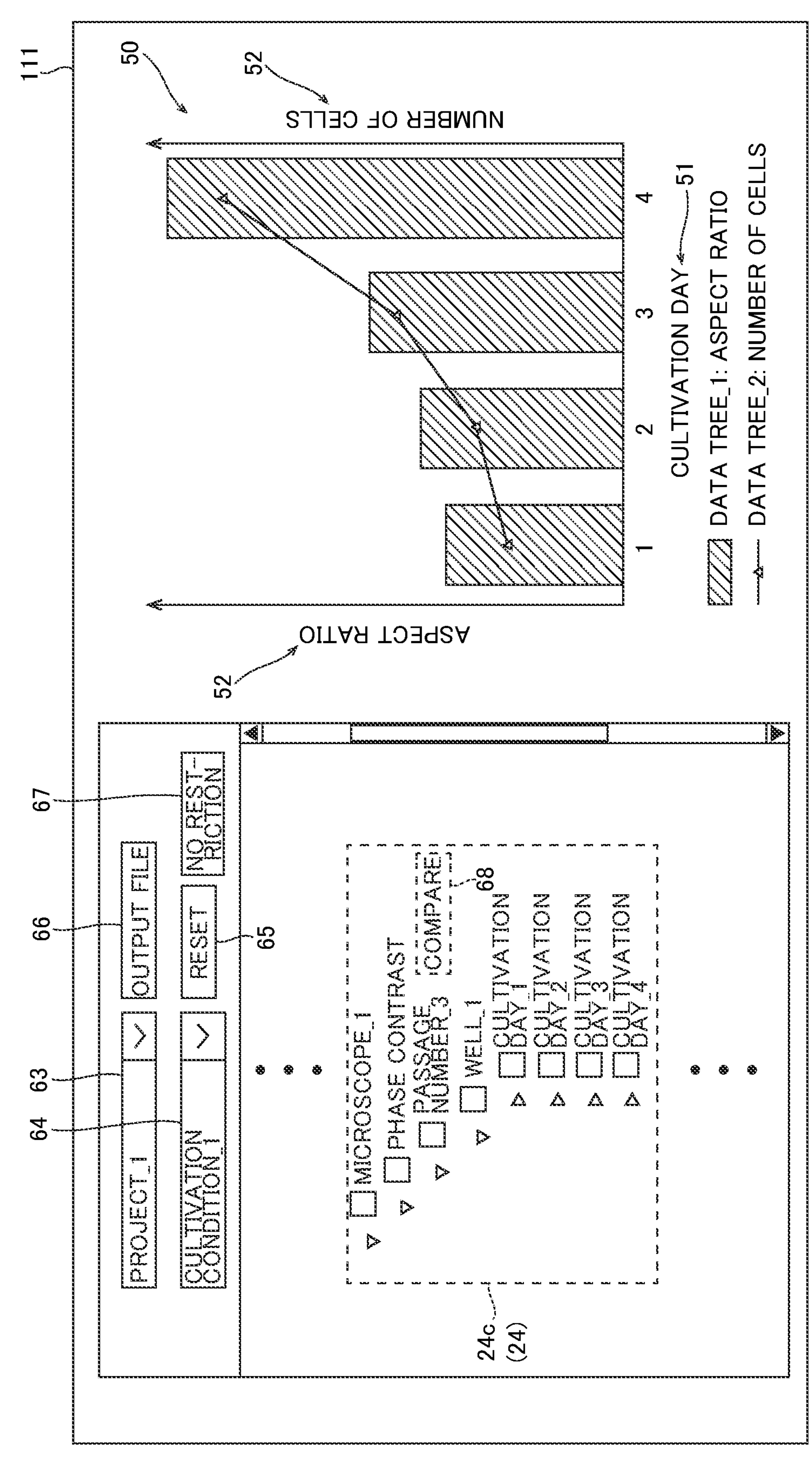
FIG. 8 is a diagram illustrating a process for comparing data trees having different vertical axis parameters with each other of the cell image analysis apparatus according to the one embodiment.

In this embodiment, as shown in FIG. 8, the display controller 13 is configured to display a third data tree 24*c* that is different from the first data tree 24*a* and has the horizontal axis parameter 51, which is common to the first data tree 24*a*, and a vertical axis parameter 52 that is different from the first data tree in the plurality of data trees 24 stored in the storage 20 to be selectable by the user, and, when the third data tree 24*c* is selected by the user, to update the graph 50 by adding the analysis results of the cell images 30 that are included in the third data tree 24*c* selected by the user to the graph 50. Based on the updated graph 50, the user can check correlation of analysis results between data trees 24 having different vertical axis parameters 52.

Specifically, the display controller 13 is configured to display an indication item 68 "No Restriction" for allowing the user to select the third data tree 24*c* to display the third data tree on the display 111. Also, the display controller 13 is configured to, if the indication item 67 "No Restriction" on the display 111 is selected in accordance with an instruction input through the input 112 by the user, remove a restriction that restricts the search for the second data tree 24*b* within a condition that the second data tree has the horizontal axis parameter 51 and the vertical axis parameter 52 common to the first data tree 24*a* so as to display the plurality of data trees 24 stored in the storage 20 on the display 111 so as to be selectable by the user. The user can select the third data tree 24*c* that has the horizontal axis parameter 51 common to the first data tree 24*a* and the vertical axis parameter 52 different from the first data tree in the data trees 24 that are displayed on the display 111.

Also, the display controller 13 is configured to display, on the display 111, an indication item 68 "Compare" corresponding to an instruction of the user to add the analysis results of the cell images 30 that are included in the third data tree 24*c* to the graph 50. Specifically, the graph creator 12 is configured to re-create the graph 50, if the indication item 68 "Compare" on the screen of the display 111 is selected in accordance with an instruction input through the input 112 by the user, by adding the analysis results of the cell images 30 that are included in the third data tree 24*c* selected by the user to the graph 50. Also, the display controller 13 is configured to transmit the graph 50 re-created by the graph creator 12 to the computer 110 so as to update the graph 50 displayed on the display 111. For example, the graph 50 updated has the vertical axis parameter 52 (aspect ratio in FIG. 8) of the first data tree 24*a* on a left side of the graph, and the vertical axis parameter 52 (number of cells in FIG. 8) of the third data tree 24*c* on a right side of the graph.

Figure 9:
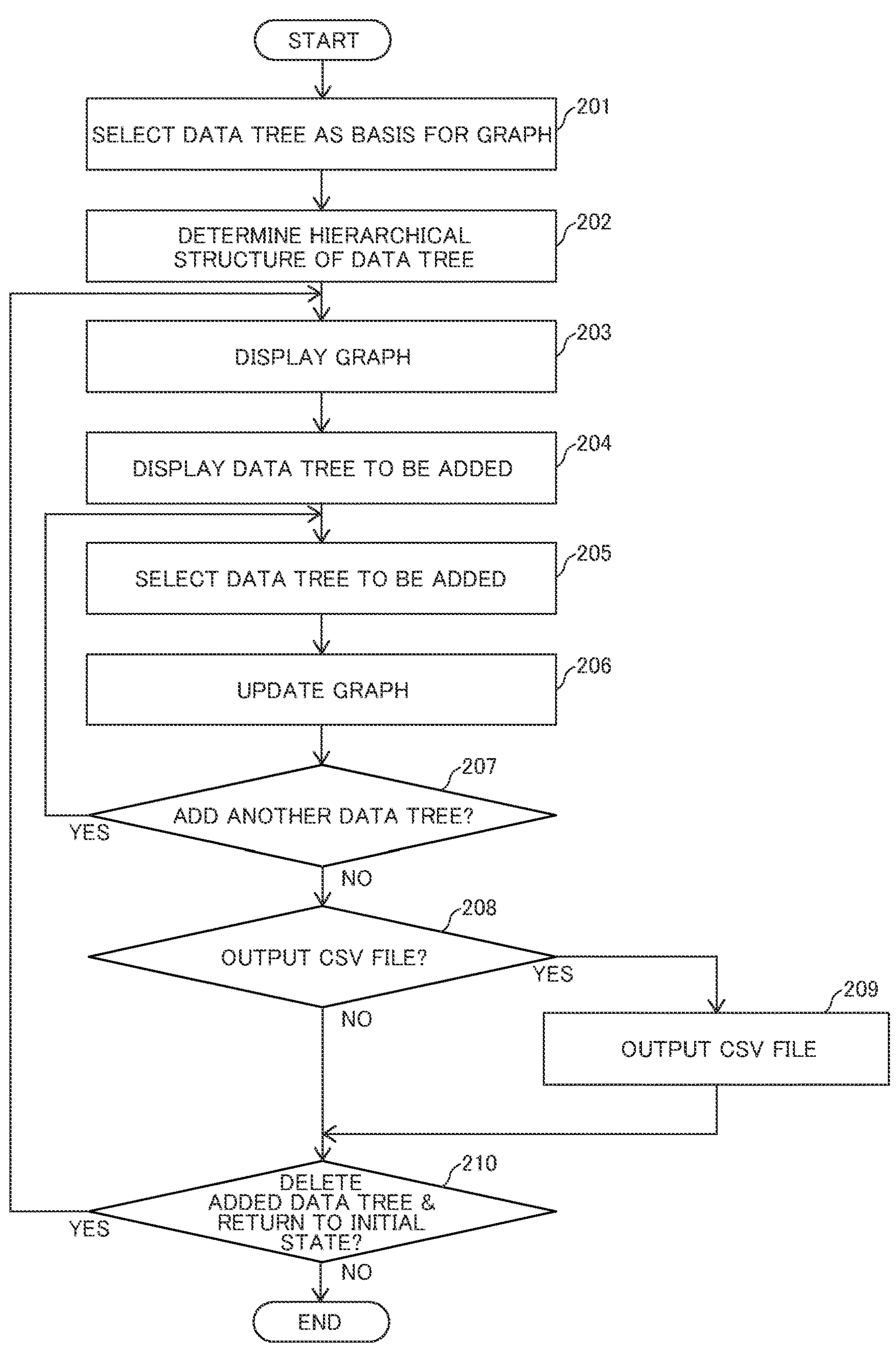
FIG. 9 is a flowchart illustrating a control process for comparing data trees with each other of the cell image analysis apparatus according to the one embodiment.

The following description describes a control process for comparing data trees 24 with each other of the cell image analysis system 100 according to this embodiment with reference to FIG. 9.

In step 201, the first data tree 24*a* that serves as a basis for the graph 50 is first selected in accordance with an instruction input through the input 112 by the user as shown in FIG. 9. Subsequently, in step 202, a hierarchical structure of the first data tree 24*a* is determined (changed) in accordance with an instruction input through the input 112 by the user. Subsequently, in step 203, the graph creator 12 creates the graph 50 relating to the first data tree 24*a*, and the display controller 13 displays the graph 50 created by the graph creator 12 on the display 111.

Subsequently, in step 204, the data tree searcher 14 searches for the second data tree 24*b*, and the display controller 13 displays the second data tree 24*b* searched by the data tree searcher 14 on the display 111. Subsequently, in step 205, the second data tree 24*b* to be added to the graph 50 is selected from the second data trees 24*b* that are displayed on the display 111 in accordance with an instruction input through the input 112 by the user. Subsequently, in step 206, the graph creator 12 re-creates the graph 50 by adding the analysis results of the cell images 30 that are included in the second data tree 24*b*, the display controller 13 displays the graph 50 re-created by the graph creator 12 on the display 111 (updates the graph 50 on the display 111).

Subsequently, in step 207, it is determined by the user whether to further add another second data tree 24*b*. If it is determined by the user to further add another second data tree 24*b* in step 207, the procedure goes to step 205. Subsequently, the processes of steps 205 and 206 are executed. Also, if it is determined by the user to further add another second data tree 24*b* in step 207, the procedure goes to step 208.

Subsequently, in step 208, it is determined by the user whether to output the CSV file 70. If it is determined by the user to output the CSV file 70 in step 208, the procedure goes to step 209. Subsequently, in step 209, the file output 15 outputs the CSV file 70 including the cell images 30 that serve as a basis for the graph 50, and the numerical data of the graph 50 to the computer 110. Subsequently, the procedure goes to step 210. Also, if it is not determined by the user to output the CSV file 70 in step 208, the procedure goes to step 210 without executing the process of step 209.

Subsequently, in step 210, it is determined by the user whether to delete the second data tree 24*b* that has been added to the graph 50 and to return the graph to the initial state. Subsequently, it is determined by the user to delete the second data tree 24*b* that has been added to the graph 50 and to return the graph to the initial state in step 210, the procedure goes to step 203. Subsequently, the processes of steps 203 to 209 are appropriately executed. Also, if it is not determined by the user to delete the second data tree 24*b* that has been added to the graph 50 and to return the graph to the initial state, and an instruction to end the control process is input by the user, the control process ends.

(Advantages of the Embodiment)

In this embodiment, the following advantages are obtained.

In this embodiment, as described above, a cell image analysis system 100 includes a data tree creator 11 configured to create a plurality of data trees 24 relating to cell images 30 by classifying the cell images 30 into a plurality of groups each of which includes the cell images that have common classification information 40; a storage 20 configured to store the plurality of data trees 24 created by the data tree creator 11; a graph creator 12 configured to create a graph 50 relating to a first data tree 24*a* that is selected by a user, and having classification information 40 of a bottom layer of the first data tree 24*a* as a horizontal axis parameter 51 and analysis results of the cell images 30 that are included in the first data tree 24*a* as a vertical axis parameter 52; and a display controller 13 configured to display the graph 50 created by the graph creator 12, wherein the display controller 13 is configured to display a second data tree 24*b* that is different from the first data tree 24*a* and has the horizontal axis parameter 51 and the vertical axis parameter 52 that are common to the first data tree 24*a* in the plurality of data trees 24 stored in the storage 20 to be selectable by the user, and, when the second data tree 24*b* is selected by the user, to update the graph 50 by adding the analysis results of the cell images 30 that are included in the second data tree 24*b* selected by the user to the graph 50.

Accordingly, it possible to display analysis results of the cell images 30 that are included in the first data tree 24*a*, and the analysis results of the cell images 30 that are included in the second data tree 24*b*, which is different from the first data tree 24*a* and has common horizontal and vertical axis parameters 51 and 52 to the first data tree 24*a* on the same graph 50 to compare them with each other. Consequently, it is possible to easily compare different data trees 24 with each other in a case in which cell images 30 are managed by using data trees 24.

Although it is conceivable that a user adds data of the second data tree 24*b* to the first data tree 24*a* and creates a new data tree 24 in order to compare the different data trees 24, an additional operation is required for the user to add the data of the second data tree 24*b* to the first data tree 24*a* in such a case of new data tree creation. Contrary to this, the graph 50 is updated by adding the analysis results of the cell images 30 that are included in the second data tree 24*b*, which is different from the first data tree 24*a* and has common horizontal and vertical axis parameters 51 and 52 to the first data tree 24*a*, to the graph 50 as described above. Accordingly, because the graph 50 is automatically updated when the second data tree 24*b* is selected by the user, the user can easily compare the different data trees 24 with each other without such an additional operation for adding the data of the second data tree 24*b* to the first data tree 24*a*.

Also, because the user necessarily appropriately aligns the vertical and horizontal axes of the graph 50 when comparing the different data trees 24 with each other, an additional operation is required for the user to appropriately align the vertical and horizontal axes of the graph 50 in this case. Contrary to this, the graph 50 is updated by adding the analysis results of the cell images 30 that are included in the second data tree 24*b*, which is different from the first data tree 24*a* and has common horizontal and vertical axis parameters 51 and 52 to the first data tree 24*a*, to the graph 50 as described above. Accordingly, because the graph 50 is automatically updated when the second data tree 24*b* is selected by the user, the user can easily compare the different data trees 24 with each other without such an additional operation for appropriately aligning the vertical and horizontal axes of the graph 50.

In addition, following additional advantages can be obtained by the aforementioned embodiment added with configurations discussed below.

That is, in the cell image analysis system 100 according to this embodiment, as discussed above, a data tree searcher 14 configured to search for the second data tree 24*b* in the plurality of data trees 24 stored in the storage 20 is further provided; and the display controller 13 is configured to display the second data tree 24*b* searched by the data tree searcher 14 so as to be selectable by the user. Accordingly, because the second data tree 24*b* searched by the data tree searcher 14 is shown to the user, the user can easily select the desired second data tree 24*b*.

In this embodiment, as described above, the data tree searcher 14 is configured to be able to search for the second data tree 24*b* in the plurality of data trees 24 stored in the storage 20 with the project and the cultivation conditions relating to cell cultivation being specified as search criteria; and the display controller 13 is configured to display the second data tree 24*b* searched by the data tree searcher 14 with the search criteria being specified so as to be selectable by the user. Accordingly, because the second data tree 24*b* searched by the data tree searcher 14 is shown to the user with the project and the cultivation conditions being specified as search criteria, the user can easily select the desired second data tree 24*b*.

In this embodiment, as described above, the data tree searcher 14 is configured to be able to search for the second data tree 24*b* in the plurality of data trees 24 stored in the storage 20 with a cultivation condition that is common to the first data tree 24*a* being specified as the search criterion; and the display controller 13 is configured to display the second data tree 24*b*, which corresponds to the cultivation condition that is common to the first data tree 24*a*, searched by the data tree searcher 14 with the cultivation condition that is common to the first data tree 24*a* being specified as the search criterion. Accordingly, because the second data tree 24*b* that is searched by the data tree searcher 14 with the project and the cultivation conditions common to the first data tree 24*a* being specified as search criteria, and corresponds to the cultivation condition that is common to the first data tree 24*a* is shown, the user can easily select the desired second data tree 24*b* corresponding to the cultivation condition that is common to the first data tree 24*a*, which is often desired for comparison by the user.

In this embodiment, as described above, the display controller 13 is configured to update the graph 50 by adding the analysis results of the cell images 30 that are included in the second data tree 24*b* selected by the user in a color different from the analysis results of the cell images 30 that are included in the first data tree 24*a* to the graph 50. Accordingly, because the user can easily visually distinguish between the analysis results of the cell images 30 that are included in the second data tree 24*b* and the analysis results of the cell images 30 that are included in the first data tree 24*a*, the user can easily compare the data trees 24 with each other.

In this embodiment, as described above, the display controller 13 is configured to update the graph 50, if the user provides an instruction to delete the analysis results that are included in the second data tree 24*b* and have been added to the graph 50, by deleting the analysis results of the cell images 30 that are included in the second data tree 24*b* and have been added to the graph 50 from the graph 50.

Accordingly, if the analysis results of the cell images 30 that are included in the second data tree 24*b* and have been added to the graph 50 becomes unnecessary for comparison, the unnecessary analysis results of the cell images 30 that are included in the second data tree 24*b* can be deleted from the graph 50.

In this embodiment, as described above, the horizontal axis parameter 51 is accessory information on cell cultivation or imaging. Accordingly, because the horizontal axis parameter 51 is accessory information on cell cultivation or imaging, the horizontal axis parameter 51 can be appropriately specified.

In this embodiment, as described above, the vertical axis parameter 52 corresponds to feature amounts based on the cell images 30. Accordingly, because the vertical axis parameter 52 corresponds to feature amounts based on the cell images 30, the vertical axis parameter 52 can be appropriately specified.

In this embodiment, as described above, the data tree 24 is formed as a virtual data tree 24 having a hierarchical structure on a display screen. Accordingly, dissimilar to a case in which the data tree 24 is formed by forming a folder having a hierarchical structure, an additional complicated operation such as reformation of the folder is not required to change the hierarchical structure. Consequently, it is possible to manage the cell images 30 by using data trees 24 without such an additional complicated operation.

In this embodiment, as discussed above, the cell image analysis system 100 further includes a file output 15 configured to output the cell images 30 that serve as a basis for the graph 50 including the added analysis results of the cell images 30 that are included in the second data tree 24*b*, and the graph 50 that includes the added analysis results of the cell images 30 that are included in the second data tree 24*b* as a CSV file 70. Accordingly, because the cell images 30 and the graph 50 that form a comparison result can be output as the versatile CSV file 70, data of the comparison result (CSV file 70) can be easily edited and the data of the comparison result (CSV file 70) can be easily sent between users.

In this embodiment, as discussed above, the file output 15 is configured to output the CSV file 70 with additional information including information on at least one of a project and a cultivation condition relating to cell cultivation. Accordingly, the user can check the project and the cultivation condition only based on the CSV file 70 in operations using the CSV file 70. Consequently, it is possible to avoid an additional operation for checking the project and the cultivation condition by using a file other than the CSV file 70.

In this embodiment, as discussed above, the display controller 13 is configured to display a third data tree 24*c* that is different from the first data tree 24*a* and has the horizontal axis parameter 51, which is common to the first data tree 24*a*, and a vertical axis parameter 52 that is different from the first data tree in the plurality of data trees 24 stored in the storage 20 to be selectable by the user, and, when the third data tree 24*c* is selected by the user, to update the graph 50 by adding the analysis results of the cell images 30 that are included in the third data tree 24*c* selected by the user to the graph 50. Accordingly, it is possible to display not only the data trees 24 (first data tree 24*a* and second data tree 24*b*) that have the same vertical axis parameter 52 but also the data trees 24 (first data tree 24*a* and third data tree 24*c*) that have different vertical axis parameter 52 on the same graph 50 to be compared with each other. Consequently, it is possible to improve a degree of freedom of comparison between the analysis results of the cell images 30 for the user.

Modified Embodiments

Note that the embodiment disclosed this time must be considered as illustrative in all points and not restrictive. The scope of the present invention is not shown by the above description of the embodiments but by the scope of claims for patent, and all modifications (modified embodiments) within the meaning and scope equivalent to the scope of claims for patent are further included.

Figure 10:
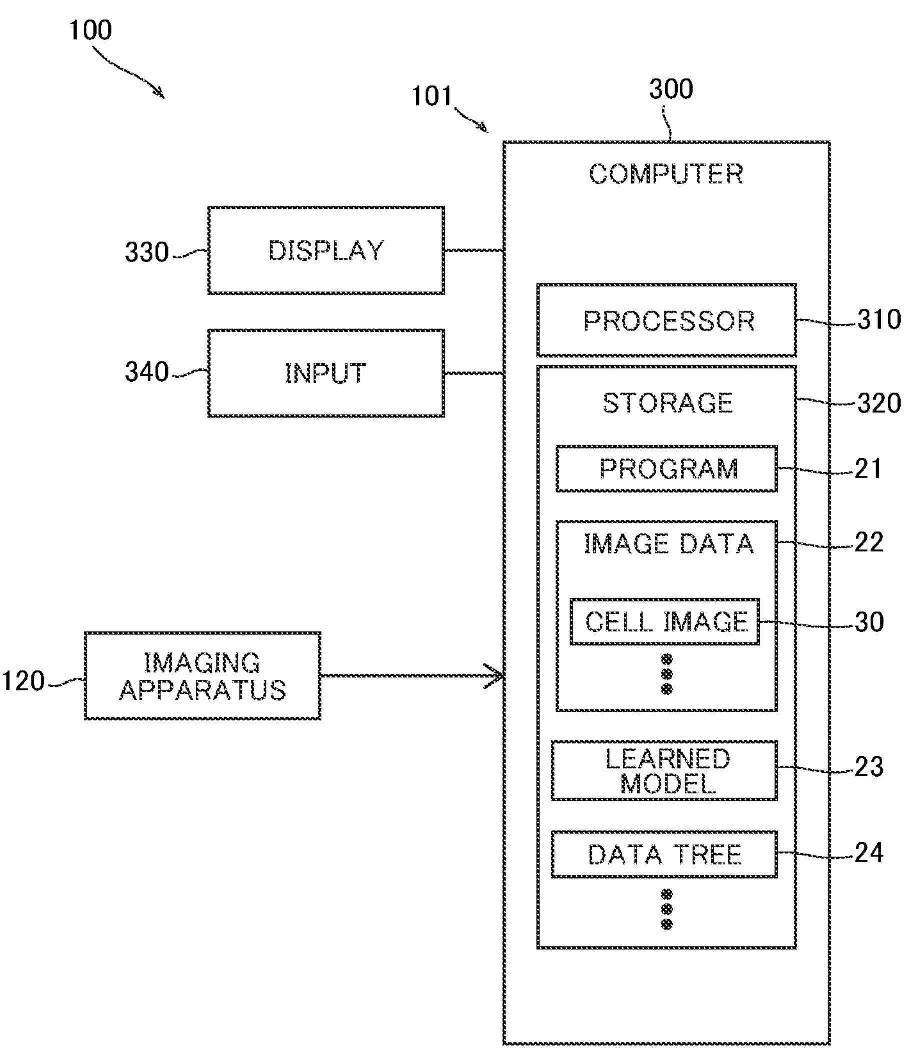
FIG. 10 is a block diagram showing a cell image analysis system according to a modified example of the one embodiment.

While the example in which the cell image analysis apparatus serves as a server in the cell image analysis system constructed of a client-server model has been shown in the aforementioned embodiment, the present invention is not limited to this. In the present invention, cell image analysis apparatus can be constructed of an independent computer, for example, as shown in FIG. 10. The cell image analysis apparatus 101 according to a modified embodiment of FIG. 10 includes a computer 300 including a processor 310 and a storage 320. A display 330 and an input 340 are connected to the computer 300. The computer 300 is connected to and can communicate with an imaging apparatus 120. The processor 310 of the computer 300 includes a data tree creator 11, a graph creator 12, and a display controller 13, a data tree searcher 14, and a file output 15, which are described in the aforementioned embodiment, as function blocks. The storage 320 is an example of the "data tree storage" in the claims.

While the example in which the single processor is configured to execute all functions (functions of the data tree creator, the graph creator, the display controller, the data tree searcher, and the file output) has been shown in the aforementioned embodiment and in the modified embodiment shown in FIG. 10, the present invention is not limited to this. Alternatively, a plurality of processors can share the aforementioned processes applied to the cell images in the present invention. Alternatively, each process can be executed by one of the processors. The plurality of processors can be included in independent computers. In other words, the cell image analysis apparatus can be constructed of a plurality of computers for executing image processing.

While the example in which the cell image analysis system includes the display has been shown in the aforementioned embodiment, the present invention is not limited to this. For example, the cell image analysis system does not necessarily include the display. In a case in which the cell image analysis system does not include the display, the processor can be configured to output display information to an external display.

While the example in which the graph creator configured to create a graph relating to a first data tree, and having classification information of a bottom layer of the first data tree as a horizontal axis parameter and analysis results of the cell images that are included in the first data tree as a vertical axis parameter has been shown in the aforementioned embodiment, the present invention is not limited to this. For example, alternatively, the graph creator can be configured to create a graph relating to the first data tree, and having classification information of a second layer from the bottom layer of the first data tree as a horizontal axis parameter and analysis results of the cell images that are included in the first data tree as a vertical axis parameter.

While the example in which the cell image analysis system (cell image analysis apparatus) includes the data tree searcher has been shown in the aforementioned embodiment, the present invention is not limited to this. For example, the cell image analysis system (cell image analysis apparatus) does not necessarily include the data tree searcher. In this case, the display controller can display data trees stored in the storage without searching so that the user can select the second data tree from the data trees displayed. However, from the viewpoint of user convenience, it is preferable that the cell image analysis system (cell image analysis device) include the data tree searcher.

While the example in which the data tree searcher is configured to be able to search for the second data tree with the project and the cultivation condition being specified as search criteria has been shown in the aforementioned embodiment, the present invention is not limited to this. In the present invention, alternatively, the data tree searcher can be configured to be able to search for the second data tree with one of the project and the cultivation condition being specified as a search criterion. Alternatively, the data tree searcher can be configured to be able to search for the second data tree with a condition other than the project and the cultivation conditions being specified as a search criterion.

While the example in which the display controller is configured to update the graph, if the user provides an instruction to delete the analysis results that are included in the second data tree and have been added to the graph, by deleting all the analysis results of the cell images that are included in the second data tree and have been added to the graph from the graph has been shown in the aforementioned embodiment, the present invention is not limited to this. In the present invention, alternatively, the display controller can be configured to update the graph, if the user provides an instruction to delete the analysis results that are included in the second data tree and have been added to the graph, by deleting some (one selected by the user, latest added one, etc.) of the analysis results of the cell images that are included in the second data tree and have been added to the graph from the graph.

While the example in which the cell image analysis system (cell image analysis apparatus) includes the file output has been shown in the aforementioned embodiment, the present invention is not limited to this. For example, the cell image analysis system (cell image analysis apparatus) does not necessarily include the file output. However, from the viewpoint of user convenience, it is preferable that the cell image analysis system (cell image analysis device) include the file output.

While the example in which the display controller is configured to display a plurality of data trees stored in the storage so that the user can select the third data tree has been shown in the aforementioned embodiment, the present invention is not limited to this. For example, alternatively, the data tree searcher can be configured to be able to search for the third data tree that has the horizontal axis parameter common to the first data tree and the vertical axis parameter different from the first data tree. In this case, the display controller can be configured to display the third data tree searched by the data tree searcher so as to be selectable by the user.

While the example in which the display controller is configured to display the third data tree so as to be selectable by the user has been shown in the aforementioned embodiment, the present invention is not limited to this. In the present invention, the display controller is not necessarily configured to display the third data tree so as to be selectable by the user as long as the first data tree is displayed so as to be selectable by the user.

[Modes]

The aforementioned exemplary embodiment will be understood as concrete examples of the following modes by those skilled in the art.

(Mode Item 1)

A cell image analysis system includes a data tree creator configured to create a plurality of data trees relating to cell images by classifying the cell images into a plurality of groups each of which includes the cell images that have common classification information; a data tree storage configured to store the plurality of data trees created by the data tree creator, and a data tree storage area that stores the data trees created by the data tree creator; a graph creator configured to create a graph relating to a first data tree that is selected by a user, and having classification information of a bottom layer or a second layer from the bottom layer of the first data tree as a horizontal axis parameter and analysis results of the cell images that are included in the first data tree as a vertical axis parameter; and a display controller configured to display the graph created by the graph creator, wherein the display controller is configured to display a second data tree that is different from the first data tree and has common horizontal and vertical axis parameters to the first data tree in the plurality of data trees stored in the data tree storage to be selectable by the user, and, when the second data tree is selected by the user, to update the graph by adding the analysis results of the cell images that are included in the second data tree selected by the user to the graph.

(Mode Item 2)

In the cell image analysis system according to mode item 1, a data tree searcher configured to search for the second data tree in the plurality of data trees stored in the data tree storage is further provided; and the display controller is configured to display the second data tree searched by the data tree searcher so as to be selectable by the user.

(Mode Item 3)

In the cell image analysis system according to mode item 2, the data tree searcher is configured to be able to search for the second data tree in the plurality of data trees stored in the data tree storage with at least one of a project and a cultivation condition relating to cell cultivation being specified as a search criterion; and the display controller is configured to display the second data tree searched by the data tree searcher with the search criterion being specified to be selectable by the user.

(Mode Item 4)

In the cell image analysis system according to mode item 3, the data tree searcher is configured to be able to search for the second data tree in the plurality of data trees stored in the data tree storage with a cultivation condition that is common to the first data tree being specified as the search criterion; and the display controller is configured to display the second data tree, which corresponds to the cultivation condition that is common to the first data tree, searched by the data tree searcher with the cultivation condition that is common to the first data tree being specified as the search criterion.

(Mode Item 5)

In the cell image analysis system according to any of mode items 1 to 4, the display controller is configured to update the graph by adding the analysis results of the cell images that are included in the second data tree selected by the user in a color different from the analysis results of the cell images that are included in the first data tree to the graph.

(Mode Item 6)

In the cell image analysis system according to any of mode items 1 to 5, the display controller is configured to update the graph, when the user provides an instruction to delete the analysis results that are included in the second data tree and have been added to the graph, by deleting the analysis results of the cell images that are included in the second data tree and have been added to the graph from the graph.

(Mode Item 7)

In the cell image analysis system according to any of mode items 1 to 6, the horizontal axis parameter is accessory information on cell cultivation or imaging.

(Mode Item 8)

In the cell image analysis system according to any of mode items 1 to 7, the vertical axis parameter corresponds to feature amounts based on the cell images.

(Mode Item 9)

In the cell image analysis system according to any of mode items 1 to 8, the data tree is formed as a virtual data tree having a hierarchical structure on a display screen.

(Mode Item 10)

In the cell image analysis system according to any of mode items 1 to 9, a file output configured to output the cell images that serve as a basis for the graph including the added analysis results of the cell images that are included in the second data tree, and the graph that includes the added analysis results of the cell images that are included in the second data tree as a CSV file is further provided.

(Mode Item 11)

In the cell image analysis system according to mode item 10, the file output is configured to output the CSV file with additional information including information on at least one of a project and a cultivation condition relating to cell cultivation.

(Mode Item 12)

In the cell image analysis system according to any of mode items 1 to 11, the display controller is configured to display a third data tree that is different from the first data tree and has a common horizontal axis parameter to the first data tree and a vertical axis parameter different from the first data tree in the plurality of data trees stored in the data tree storage to be selectable by the user, and, when the third data tree is selected by the user, to update the graph by adding the analysis results of the cell images that are included in the third data tree selected by the user to the graph.

DESCRIPTION OF REFERENCE NUMERALS

11; data tree creator
12; graph creator
13; display controller
14; data tree searcher
15; file output
20, 320; storage (data tree storage)
24; data tree
24*a*; first data tree
24*b*; second data tree
24*c*; third data tree
30; cell image
40; classification information
50; graph
51; horizontal axis parameter
52; vertical axis parameter
70; CSV file
100; cell image analysis system

The invention claimed is:

1. A cell image analysis system comprising:

a data tree creator configured to create a plurality of data trees relating to cell images by classifying the cell images into a plurality of groups each of which includes the cell images that have common classification information;

a data tree storage configured to store the plurality of data trees created by the data tree creator;

a graph creator configured to create a graph relating to a first data tree that is selected by a user, and having classification information of a bottom layer or a second layer from the bottom layer of the first data tree as a horizontal axis parameter and analysis results of the cell images that are included in the first data tree as a vertical axis parameter; and a display controller configured to display the graph created by the graph creator, a data tree searcher configured to search for a second data tree from among the plurality of data trees stored in the data tree storage based on a search condition relating to cell culture and different from classification information, wherein the display controller is configured to display the second data tree that is different from the first data tree and has common horizontal and vertical axis parameters to the first data tree in the plurality of data trees stored in the data tree storage to be selectable by the user, and, when the second data tree is selected by the user, to update the graph by adding the analysis results of the cell images that are included in the second data tree selected by the user to the graph.

2. The cell image analysis system according to claim 1, wherein the display controller is configured to display the second data tree searched by the data tree searcher so as to be selectable by the user.

3. The cell image analysis system according to claim 2, wherein the data tree searcher is configured to be able to search for the second data tree in the plurality of data trees stored in the data tree storage with at least one of a project and a cultivation condition relating to cell cultivation being specified as a search criterion; and the display controller is configured to display the second data tree searched by the data tree searcher with the search criterion being specified to be selectable by the user.

4. The cell image analysis system according to claim 3, wherein the data tree searcher is configured to be able to search for the second data tree in the plurality of data trees stored in the data tree storage with a cultivation condition that is common to the first data tree being specified as the search criterion; and the display controller is configured to display the second data tree, which corresponds to the cultivation condition that is common to the first data tree, searched by the data tree searcher with the cultivation condition that is common to the first data tree being specified as the search criterion.

5. The cell image analysis system according to claim 1, wherein the display controller is configured to update the graph by adding the analysis results of the cell images that are included in the second data tree selected by the user in a color different from the analysis results of the cell images that are included in the first data tree to the graph.

6. The cell image analysis system according to claim 1, wherein the display controller is configured to update the graph, when the user provides an instruction to delete the analysis results that are included in the second data tree and have been added to the graph, by deleting the analysis results of the cell images that are included in the second data tree and have been added to the graph from the graph.

7. The cell image analysis system according to claim 1, wherein the horizontal axis parameter is accessory information on cell cultivation or imaging.

8. The cell image analysis system according to claim 1, wherein the vertical axis parameter corresponds to feature amounts based on the cell images.

9. The cell image analysis system according to claim 1, wherein the data tree is formed as a virtual data tree having a hierarchical structure on a display screen.

10. The cell image analysis system according to claim 1 further comprising a file output configured to output the cell images that serve as a basis for the graph including the added analysis results of the cell images that are included in the second data tree, and the graph that includes the added analysis results of the cell images that are included in the second data tree as a Comma Separated Value (CSV) file.

11. The cell image analysis system according to claim 10, wherein the file output is configured to output the CSV file with additional information including information on at least one of a project and a cultivation condition relating to cell cultivation.

12. The cell image analysis system according to claim 1, wherein the display controller is configured to display a third data tree that is different from the first data tree and has a common horizontal axis parameter to the first data tree and a vertical axis parameter different from the first data tree in the plurality of data trees stored in the data tree storage to be selectable by the user, and, when the third data tree is selected by the user, to update the graph by adding the analysis results of the cell images that are included in the third data tree selected by the user to the graph.

* * * * *